(12) United States Patent
Banet

(10) Patent No.: US 7,179,228 B2
(45) Date of Patent: *Feb. 20, 2007

(54) CUFFLESS SYSTEM FOR MEASURING BLOOD PRESSURE

(75) Inventor: Matthew J Banet, Del Mar, CA (US)

(73) Assignee: Triage Wireless, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/709,014

(22) Filed: Apr. 7, 2004

(65) Prior Publication Data

US 2005/0228296 A1    Oct. 13, 2005

(51) Int. Cl.
*A61B 5/02* (2006.01)

(52) U.S. Cl. ............ 600/485; 600/500; 600/503; 600/504; 600/506

(58) Field of Classification Search ........... 600/300, 600/301, 485–507
See application file for complete search history.

(56) References Cited

U.S. PATENT DOCUMENTS

| | | | |
|---|---|---|---|
| 3,412,729 A | 11/1968 | Smith | |
| 4,063,551 A | 12/1977 | Sweeney | |
| 4,080,966 A | 3/1978 | McNally et al. | |
| 4,320,767 A | 3/1982 | Villa-Real | |
| 4,367,752 A | 1/1983 | Jimenez et al. | |
| 4,380,240 A | 4/1983 | Jobsis et al. | |
| 4,425,920 A | 1/1984 | Bourland et al. | |
| 4,669,485 A * | 6/1987 | Russell | 600/492 |
| 4,681,118 A | 7/1987 | Asai et al. | |
| 4,777,954 A | 10/1988 | Keusch et al. | |
| 4,825,879 A | 5/1989 | Tan et al. | |
| 4,846,189 A | 7/1989 | Sun | |
| 4,869,261 A | 9/1989 | Penaz | |
| 4,917,108 A | 4/1990 | Mault | |
| 5,002,055 A | 3/1991 | Merki et al. | |
| 5,038,792 A | 8/1991 | Mault | |
| 5,054,494 A * | 10/1991 | Lazzaro et al. | 600/490 |
| 5,111,817 A | 5/1992 | Clark et al. | |
| 5,140,990 A | 8/1992 | Jones | |
| 5,178,155 A | 1/1993 | Mault | |
| 5,179,958 A | 1/1993 | Mault | |
| 5,213,099 A | 5/1993 | Tripp, Jr. | |
| 5,237,997 A * | 8/1993 | Greubel et al. | 600/485 |
| 5,297,554 A * | 3/1994 | Glynn et al. | 600/476 |
| 5,309,916 A * | 5/1994 | Hatschek | 600/485 |
| 5,316,008 A * | 5/1994 | Suga et al. | 600/513 |
| 5,368,039 A | 11/1994 | Moses | |
| 5,435,315 A | 7/1995 | McPhee et al. | |
| 5,485,848 A | 1/1996 | Jackson et al. | |

(Continued)

OTHER PUBLICATIONS

Claims from U.S. Appl. No. 10/709015 to Banet et al.*

(Continued)

*Primary Examiner*—Charles Marmor, II.
*Assistant Examiner*—Patricia Mallari

(57) ABSTRACT

The invention provides a device that measures a patient's blood pressure without using an inflatable cuff. The device includes an optical module featuring an optical source and a first optical sensor that generates a first set of information; a flexible, thin-film pressure sensor that generates a second set of information; and a processing module, configured to receive and process the first and second sets of information to calculate a time-dependent blood pressure value.

16 Claims, 12 Drawing Sheets

U.S. PATENT DOCUMENTS

| | | | | |
|---|---|---|---|---|
| 5,551,438 | A | 9/1996 | Moses | |
| 5,632,272 | A | 5/1997 | Diab et al. | |
| 5,649,543 | A * | 7/1997 | Hosaka et al. | 600/493 |
| 5,727,558 | A | 3/1998 | Hakki et al. | |
| 5,743,857 | A | 4/1998 | Shinoda et al. | |
| 5,752,920 | A * | 5/1998 | Ogura et al. | 600/494 |
| 5,788,634 | A * | 8/1998 | Suda et al. | 600/382 |
| 5,836,300 | A | 11/1998 | Mault | |
| 5,857,975 | A | 1/1999 | Golub | |
| 5,865,755 | A | 2/1999 | Golub | |
| 5,865,758 | A | 2/1999 | Louzianine | |
| 5,891,042 | A | 4/1999 | Sham et al. | |
| 5,921,936 | A | 7/1999 | Inukai et al. | |
| 5,964,701 | A * | 10/1999 | Asada et al. | 600/300 |
| 6,004,274 | A | 12/1999 | Nolan et al. | |
| 6,013,009 | A | 1/2000 | Karkanen | |
| 6,027,455 | A * | 2/2000 | Inukai et al. | 600/490 |
| 6,050,940 | A | 4/2000 | Braun | |
| 6,093,146 | A * | 7/2000 | Filangeri | 600/300 |
| 6,095,985 | A * | 8/2000 | Raymond et al. | 600/513 |
| 6,176,831 | B1 | 1/2001 | Voss et al. | |
| 6,224,548 | B1 | 5/2001 | Gopinathan et al. | |
| 6,245,014 | B1 | 6/2001 | Brainard, II | |
| 6,272,936 | B1 | 8/2001 | Oreper | |
| 6,280,390 | B1 | 8/2001 | Akselrod et al. | |
| 6,331,162 | B1 * | 12/2001 | Mitchell | 600/485 |
| 6,334,065 | B1 | 12/2001 | Al-Ali et al. | |
| 6,336,900 | B1 | 1/2002 | Alleckson | |
| 6,364,842 | B1 | 4/2002 | Amano | |
| 6,371,921 | B1 | 4/2002 | Caro et al. | |
| 6,375,614 | B1 | 4/2002 | Braun | |
| 6,398,727 | B1 | 6/2002 | Bui | |
| 6,413,223 | B1 | 7/2002 | Yang | |
| 6,432,061 | B1 | 8/2002 | Nissila et al. | |
| 6,443,905 | B1 | 9/2002 | Nissila et al. | |
| 6,443,906 | B1 * | 9/2002 | Ting et al. | 600/490 |
| 6,475,146 | B1 | 11/2002 | Frelburger et al. | |
| 6,475,153 | B1 | 11/2002 | Khair et al. | |
| 6,477,397 | B1 | 11/2002 | Ronkainen et al. | |
| 6,511,436 | B1 | 1/2003 | Asmar | |
| 6,514,211 | B1 | 2/2003 | Baura | |
| 6,527,711 | B1 | 3/2003 | Stivoric et al. | |
| 6,533,729 | B1 * | 3/2003 | Khair et al. | 600/503 |
| 6,546,269 | B1 | 4/2003 | Kurnik | |
| 6,553,247 | B1 | 4/2003 | Rytky | |
| 6,556,852 | B1 | 4/2003 | Schulze et al. | |
| 6,558,321 | B1 | 5/2003 | Burd et al. | |
| 6,571,200 | B1 | 5/2003 | Mault | |
| 6,595,929 | B2 | 7/2003 | Stivoric et al. | |
| 6,599,251 | B2 | 7/2003 | Chen et al. | |
| 6,605,038 | B1 | 8/2003 | Teller | |
| 6,605,044 | B2 | 8/2003 | Bimbaum | |
| 6,609,023 | B1 | 8/2003 | Fischell | |
| 6,612,984 | B1 | 9/2003 | Kerr, II | |
| 6,616,613 | B1 * | 9/2003 | Goodman | 600/504 |
| 6,645,154 | B2 | 11/2003 | Oka | |
| 6,645,155 | B2 | 11/2003 | Inukai et al. | |
| 6,652,466 | B2 | 11/2003 | Sugo et al. | |
| 6,676,608 | B1 * | 1/2004 | Keren | 600/481 |
| 6,678,543 | B2 | 1/2004 | Diab et al. | |
| 6,681,454 | B2 | 1/2004 | Modgil et al. | |
| 6,700,174 | B1 * | 3/2004 | Miu et al. | 257/419 |
| 6,714,804 | B2 | 3/2004 | Al-Ali et al. | |
| 6,723,054 | B1 | 4/2004 | Baruch et al. | |
| 6,740,045 | B2 | 5/2004 | Amano | |
| 6,775,566 | B2 | 8/2004 | Nissila | |
| 6,808,473 | B2 | 10/2004 | Hisano et al. | |
| 6,813,511 | B2 | 11/2004 | Diab et al. | |
| 6,814,705 | B2 * | 11/2004 | Kawaguchi | 600/500 |
| 6,852,083 | B2 | 2/2005 | Caro et al. | |
| 6,871,084 | B1 | 3/2005 | Kingsley et al. | |
| 2002/0183627 | A1 | 12/2002 | Nishil et al. | |
| 2004/0030261 | A1 | 2/2004 | Rantala | |
| 2004/0260186 | A1 | 12/2004 | Dekkar | |

OTHER PUBLICATIONS

"serial interface" Collins Dictionary of Computing (2000). Retrieved Mar. 21, 2005, from xreferplus. http://www.xreferplus.com/entry/1255375.*

Yang, Boo-Ho, et al., Cuff-less Continuous Monitoring of Beat-To-Beat Blood Pressure Using Sensor Fusion, submitted to IEEE transactions on Biomedical Engineering, 2000.

Yang, Boo-Ho et al., Cuff-less Continuous Monitoring of Beat-To-Beat Pressure Using Sensor Fusion, submitted to IEEE Transactions on Biomedical Engineering.

Weijia Cui, Lee E. et al., In Vivo Refectance of Blood and Tissue as a Function of Light Wavelength, submitted to IEEE Transactions on Biomedical Engineering, vol. 37, No. 6.

* cited by examiner

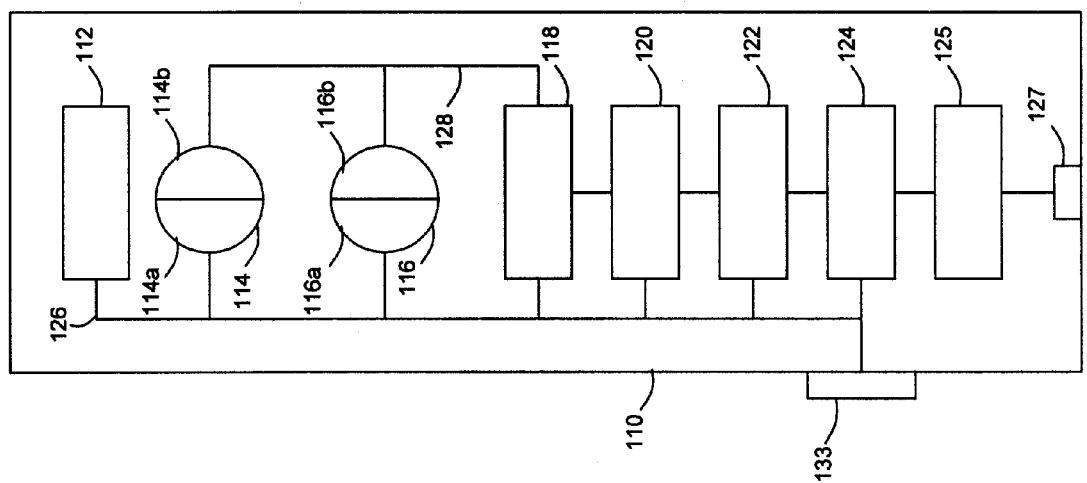

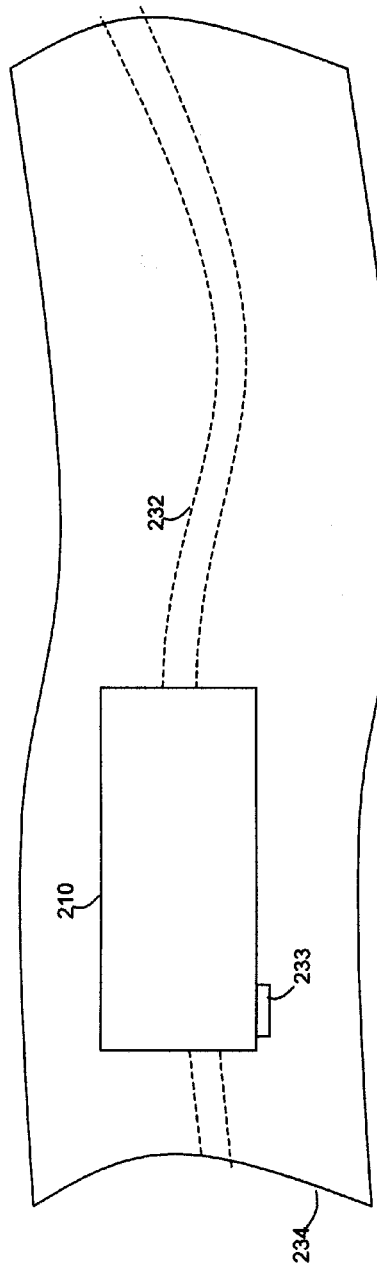
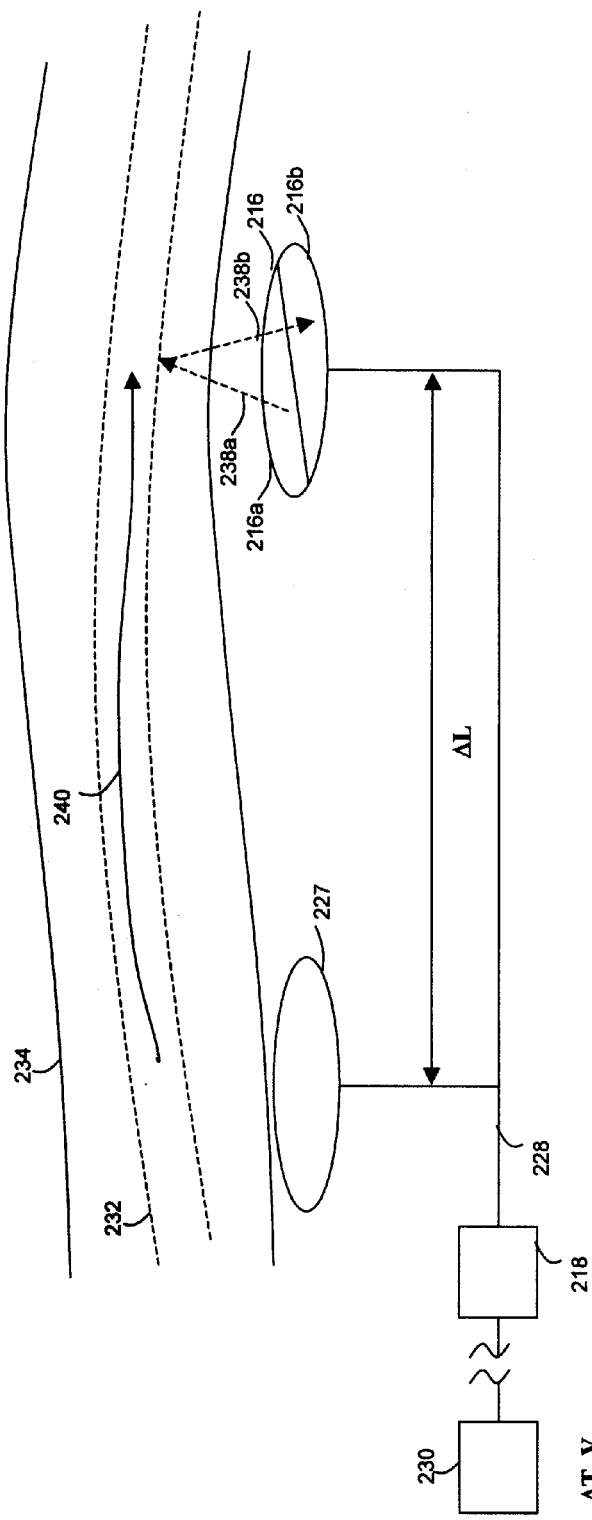

CUFFLESS SYSTEM FOR MEASURING BLOOD PRESSURE

BACKGROUND OF INVENTION

1. Field of the Invention

This invention relates to a monitor that measures blood pressure without using a cuff.

2. Description of Related Art

Blood within a patient's body is characterized by a baseline pressure value, called the diastolic pressure. Diastolic pressure indicates the pressure in an artery when the blood it contains is static. A heartbeat forces a time-dependent volume of blood through the artery, causing the baseline pressure to increase in a pulse-like manner to a value called the systolic pressure. The systolic pressure indicates a maximum pressure in a portion of the artery that contains the flowing volume of blood.

Pressure in the artery periodically increases from the diastolic pressure to the systolic pressure in a pulsatile manner, with each pulse corresponding to an individual heartbeat. Blood pressure then returns to the diastolic pressure when the flowing pulse of blood passes through the artery.

Both invasive and non-invasive devices can measure a patient's systolic and diastolic blood pressure. For example, a non-invasive medical device called a sphygmomanometer measures a patient's blood pressure using an inflatable cuff and a sensor (e.g., a stethoscope) that detects blood flow by listening for sounds called the "Korotkoff" sounds. During a measurement, a medical professional typically places the cuff around the patient's arm and inflates it to a pressure that exceeds the systolic blood pressure. The medical professional then incrementally reduces the pressure while listening for flowing blood with the stethoscope. The pressure value at which blood first begins to flow past the deflating cuff, indicated by a first Korotkoff sound (typically a "beat" or "tap" measured by the stethoscope), is the systolic pressure. The minimum pressure in the cuff that restricts blood flow is the diastolic pressure. The stethoscope monitors this pressure by detecting another Korotkoff sound, in this case a "leveling off" or disappearance in the acoustic magnitude of the periodic beats, indicating that blood flow is no longer restricted.

Low-cost, automated devices measure blood pressure with an inflatable cuff and an automated acoustic or pressure sensor that measures blood flow. The cuffs in these devices are typically fitted to measure blood pressure in a patient's arm, wrist or finger. During a measurement, the cuff is automatically inflated and then incrementally deflated while the automated pressure sensor monitors blood flow. A microcontroller in the automated device then uses this information to calculate blood pressure. Cuff-based blood-pressure measurements only determine the systolic and diastolic blood pressures; they do not measure dynamic, time-dependent blood pressure.

An invasive device for measuring blood pressure, called a tonometer, is inserted into an opening in a patient's skin and features a component that compresses an artery against a portion of bone. A pressure sensor within the tonometer then measures blood pressure in the form of a time-dependent waveform. The waveform features a baseline that indicates the diastolic pressure, and time-dependent pulses, each corresponding to individual heartbeats. The maximum value of each pulse is the systolic pressure. The rising and falling edges of each pulse correspond to pressure values that lie between the systolic and diastolic pressures.

SUMMARY OF INVENTION

The invention provides a device that measures a patient's blood pressure without using an inflatable cuff. The device includes an optical module featuring an optical source and a first optical sensor that generates a first set of information; a flexible, thin-film pressure sensor that generates a second set of information; and a processing module, configured to receive and process the first and second sets of information to calculate a time-dependent blood pressure value.

BRIEF DESCRIPTION OF DRAWINGS

The features and advantages of the present invention can be understood by reference to the following detailed description taken with the drawings, in which:

FIG. 7 is a schematic, overhead view of a blood-pressure measuring device featuring optical modules according to an alternative embodiment of the invention;

FIG. 10A is a schematic, overhead view of the blood-pressure measuring device of FIG. 9 measuring blood pressure from a patient's arm;

FIG. 10B is a schematic, side view of the single optical module and thin-film pressure sensor within the blood-pressure measuring device of FIG. 9 measuring blood pressure from a patient's arm.

DETAILED DESCRIPTION

Figure 1:
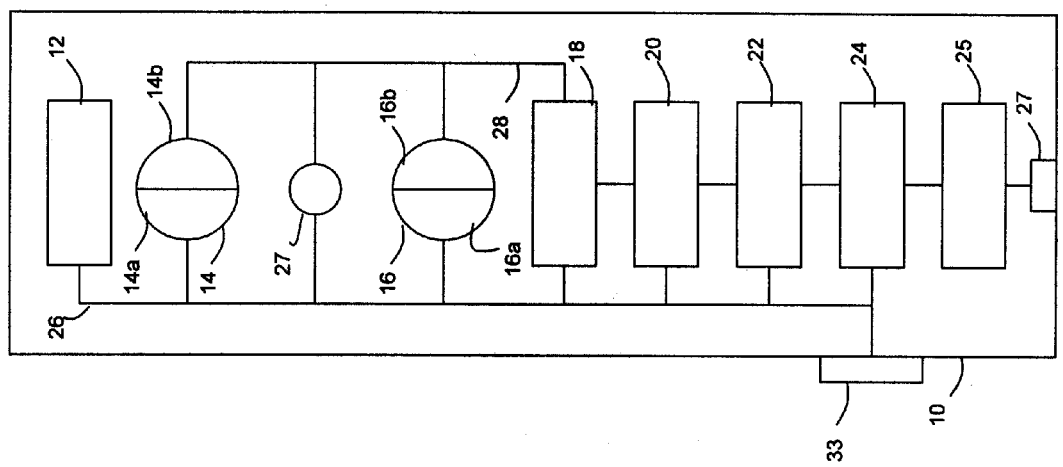
FIG. 1 is a schematic, overhead view of a blood pressure-measuring device featuring optical modules and a pressure pad according to the invention.

The following description refers to the accompanying drawings that illustrate certain embodiments of the present invention. Other embodiments are possible and modifications may be made to the embodiments without departing from the spirit and scope of the invention. Therefore, the following detailed description is not meant to limit the present invention. Rather, the scope of the present invention is defined by the appended claims.

An aspect of the invention is to provide an accurate, noninvasive, cuff-less measurement that determines a patient's blood pressure. The measurement, in different embodiments, processes waveforms generated and detected by a combination of optical modules, thin-film pressure sensors, and mechanical pressure pads to determine a time-dependent blood-pressure waveform that oscillates between diastolic and systolic blood pressure in a pulsatile manner.

The device, which can be hand-held or worn in the patient's wrist, can be used for standard applications such as routine medical check-ups, surgical procedures, or measuring blood pressure at home. Or it can be used for "telemedicine" applications based on remote monitoring since it is both cuffless and non-invasive. In this way, the invention provides a comprehensive analysis of the patient's cardiac behavior with a simple, unobtrusive device.

In one aspect, the invention provides a device that monitors a patient's blood pressure and includes: i) an optical module featuring an optical source component and a first optical sensor that generates a first set of information; ii) a flexible, thin-film pressure sensor that generates a second set of information; and iii) a processing module that receives and processes the first and second sets of information to calculate a blood pressure value.

In embodiments, the flexible, thin-film pressure sensor generates the second set of information in response to an applied force or pressure. It typically includes a sensing material featuring an electrical resistance that varies with an applied force or pressure. For example, this sensor can generate a time-dependent pressure waveform (showing, e.g., resistance) that is sent to an analog-to-digital converter for processing. The optical module further typically includes a first optical source that generates visible radiation, and a second optical source that generates infrared radiation. Radiation from these light sources is transmitted or reflected by an underlying artery, and then received by an optical sensor (e.g., a photodiode), which in response generates a photocurrent.

An analog-to-digital converter processes the photocurrent and generates a time-dependent optical waveform that, along with the time-dependent pressure waveform, yields a blood pressure value after processing by computer-readable firmware running on the processor. The firmware typically calculates systolic and diastolic blood pressure values, along with a time-dependent blood pressure, and in embodiments pulse oximetry and heart rate.

In other embodiments the device includes an adjustable band configured to attach to a user's wrist. In this case, the device features a "watch like" form factor and the adjustable band can include the flexible, thin-film pressure sensor. It can additionally attach to a finger-worn component that houses the optical module. In other embodiments, the device additionally includes a serial interface that can send (either through a wired or wireless connection) information to an external device (e.g., a computer). The serial interface can also accept information, e.g. calibration information, that is used in the calculation of blood pressure.

In another aspect, the device includes: i) a first optical module featuring a first optical source and a first optical sensor; ii) a second optical module featuring a second optical source and a second optical sensor; iii) a processing module, in electrical contact with both the first and second optical modules, that receives and processes information from the optical sensors to calculate a blood pressure value; and iv) a housing that at least partially houses both the first and second optical modules and the processing module.

In embodiments, the device can additionally include a mechanical module, typically disposed between the optical modules, which imparts and measures a pressure applied to an artery of the patient. Alternatively, the device can include an electrical impedance sensor, in place of the mechanical module, configured to measure the electrical impedance of the patient's blood.

The invention has many advantages. In particular, it provides a non-invasive, cuff-less device that measures a patient's real-time, time-dependent blood pressure. In this way, the invention combines all the benefits of conventional blood-pressure measuring devices (cuff-less, real-time measurement of a tonometer; non-invasive measurement of a sphymamometer) without any of the obvious drawbacks (e.g., uncomfortable cuffs; restrictive, invasive sensors; subjective measurement). Measurements can be made at nearly every part of the patient's body since a special, fitted cuff is not required. And since the measurement is completely unobtrusive to the patient, the device alleviates conditions, such as an uncomfortable or poorly fitting cuff, that can erroneously affect a blood-pressure measurement.

Using the same optical system for the blood-pressure measurement, the device can also measure pulse oximetry to monitor the patient's heart rate and blood oxygen saturation. These data can be used to further diagnose the patient's cardiac condition.

The device is small and makes a non-invasive blood-pressure measurement in a matter of seconds. Measurements can be made with no effect on the patient. An onboard or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure.

These same features mean the device can also be used in "telemedicine" applications where measurements are made from a remote patient and wirelessly transmitted to a central, internet-accessible computer. In this way patients with cardiac conditions can be characterized remotely over extended periods of time. This characterization, for example, can be made by a medical professional using a remote, Internet-accessible website.

With these advantageous features, medical professionals can characterize a patient's real-time blood pressure during their day-to-day activities, rather than rely on an isolated measurement during a medical check-up. This means, for example, a physician can delineate between patients exhibiting temporary increases in blood pressure during medical check-ups (sometimes called "white coat syndrome") and patients who truly have high blood pressure. With the invention physicians can determine patients who exhibit high blood pressure throughout their day-to-day activities. In response, the physician can prescribe medication and then monitor how this affects the patient's blood pressure. In general, the current invention measures blood pressure in an accurate, real-time, comprehensive manner that is not possible with conventional blood pressure-monitoring devices.

These and other advantages of the invention will be apparent from the following detailed description and from the claims.

FIG. 1 shows a hand-held blood-pressure monitoring device 10 according to the invention that provides a cuffless, non-invasive, beat-by-beat measurement of blood pressure from a patient. The device 10 features a mechanical module 27 that delivers a rapid "pressure pulse" to an underlying artery, and a pair of optical modules 14, 16, operating in a reflection mode, that measure the flow of blood in the underlying artery. A microprocessor 24 processes data measured by the optical 14, 16 and mechanical 27 modules to calculate the patient's blood pressure. The term "microprocessor" means a silicon-based microprocessor or microcontroller that can run compiled computer code to perform mathematical operations on data stored in a memory. Examples include ARM7 or ARM9 microprocessors manufactured by a number of different companies; AVR 8-bit RISC microcontrollers manufactured by Atmel; PIC CPUs manufactured by Microchip Technology Inc.; and high-end microprocessors manufactured by Intel and AMD.

A battery 12 powers both the optical modules 14, 16 and mechanical module 27 through an electrical lead 26. Each optical module 14, 16 features a light source system 14a, 16a with separate light-emitting diodes ("LEDs") that, respectively, emit optical radiation at visible ($\lambda \sim 600$ nm) and infrared ($\lambda \sim 900$ nm) wavelengths. The optical modules 14, 16 also include an optical detector system 14b, 16b that features a light-sensitive photodiode. The photodiode absorbs reflected optical radiation from both the visible and infrared LEDs, and in response generates a photocurrent that is analyzed to determine a waveform. The waveform, as described in detail below, is processed to ultimately determine the patient's blood flow and blood pressure.

The mechanical module 27 is disposed between the first 14 and second 16 optical module. It features a soft pad that delivers a rapid, calibrated pressure pulse to the underlying artery. The pressure pulse typically last as few seconds and acts to compress the artery just enough to temporarily restrict blood flow.

During a measurement, a user presses a button 33 on the device's outer surface that connects to the microprocessor 24. This process initiates the blood-pressure measurement, which consists of a first, second, and third measurement. In the first measurement, the optical modules 14, 16 measure, in a reflective optical configuration, waveforms featuring time-dependent, periodic, heartbeat-induced pulses that indicate blood flowing on both sides of the mechanical module 27. The mechanical module 27 disposed between the optical modules then delivers a gentle pressure pulse to the underlying artery to temporarily restrict the blood flow. Eventually the pressure will exceed the diastolic blood pressure, at which point the pulse amplitude in the waveform begins to decrease. This indicates the diastolic pressure.

Once this measurement is made, the second measurement commences and the mechanical module 27 delivers a second pressure pulse to the underlying artery. This pressure eventually exceeds the systolic blood pressure, causing the pulse in the waveform to eventually disappear. The microprocessor processes these data to determine the systolic blood pressure. Finally, the device makes a third measurement wherein the first 14 and second optical modules 16 measure blood flow in the absence of a pressure pulse. The third measurement yields a time-dependent waveform indicating blood flow. The microprocessor processes this waveform with the blood pressures from the first and second measurements to determine the patient's beat-by-beat blood pressure.

During the first, second, and third measurements, bone, tissue, pigmentation, and venous vessels absorb a constant amount of radiation emitted from the light source systems 14a, 16a in the optical modules 14, 16. However, flowing blood absorbs radiation in a time-dependent manner as the blood volume in the measured regions increases and then decreases with each heartbeat. The optical detector systems 14a, 16a therefore detect a "pulse", dependent on the blood flow and blood volume, when blood flows past and is measured by each optical module 14, 16.

Figure 3:
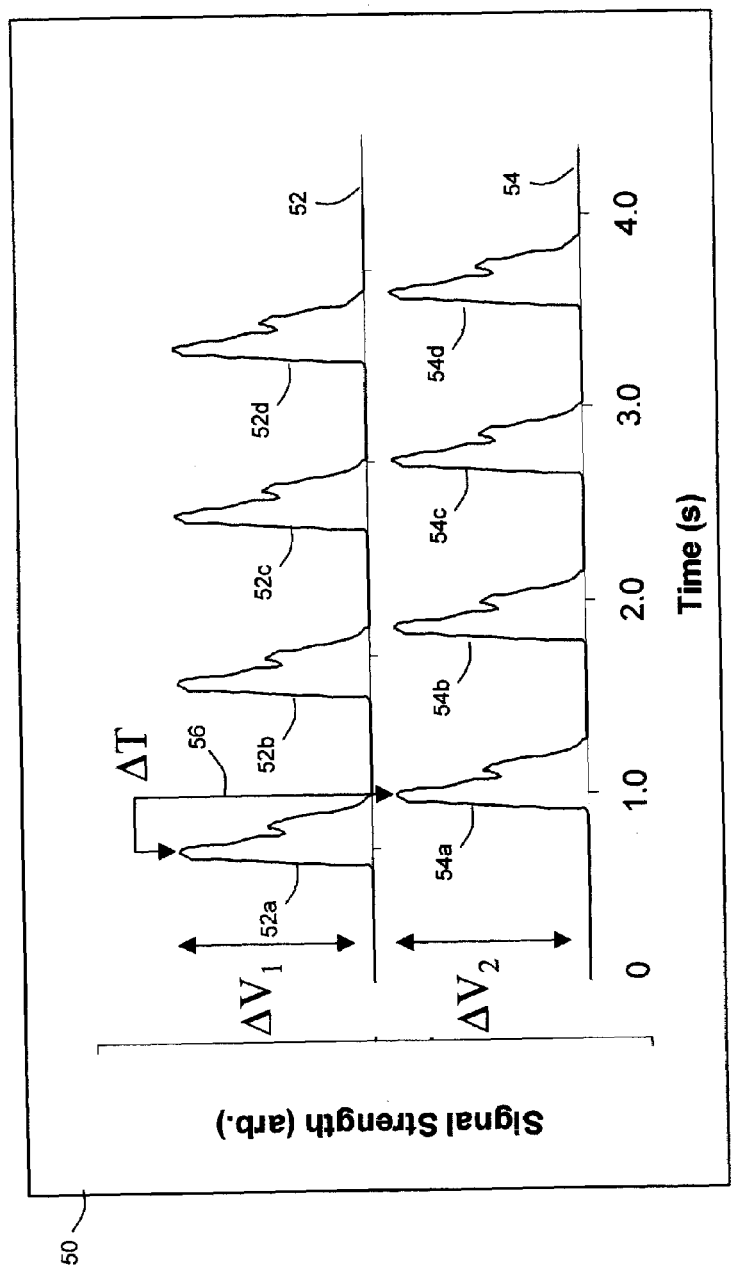
FIG. 3 is a graph showing time-dependent waveforms measured from a patient using the optical modules of FIG. 2B.

FIG. 3, for example, shows a graph 50 with first 52 and second 54 waveforms measured, respectively, by the first 14 and second 16 optical modules. The first waveform 52 includes separate pulses 52a–d, each corresponding to a different, sequential heartbeat. The second waveform 54 includes separate pulses 54a–d generated by the same heartbeat. The pulses 54a–d in the second waveform 54 lag the pulses 52a–d in the first waveform 52 by a time difference $\Delta T$ due to the physical separation ($\Delta L$) between the first and second optical modules and the patient's blood flow rate. The amplitude of each pulse ($V_1$ for the first pulse in the first waveform; $V_2$ for the first pulse in the second waveform) depends on the volume of blood flowing in the artery under the optical module.

Each optical module features an optical system that is similar to that used in a conventional pulse oximeter. These modules, in combination with the microprocessor, can thus measure pulse oximetry (also known as blood-oxygen saturation) values in addition to blood pressure.

Figure 4A:
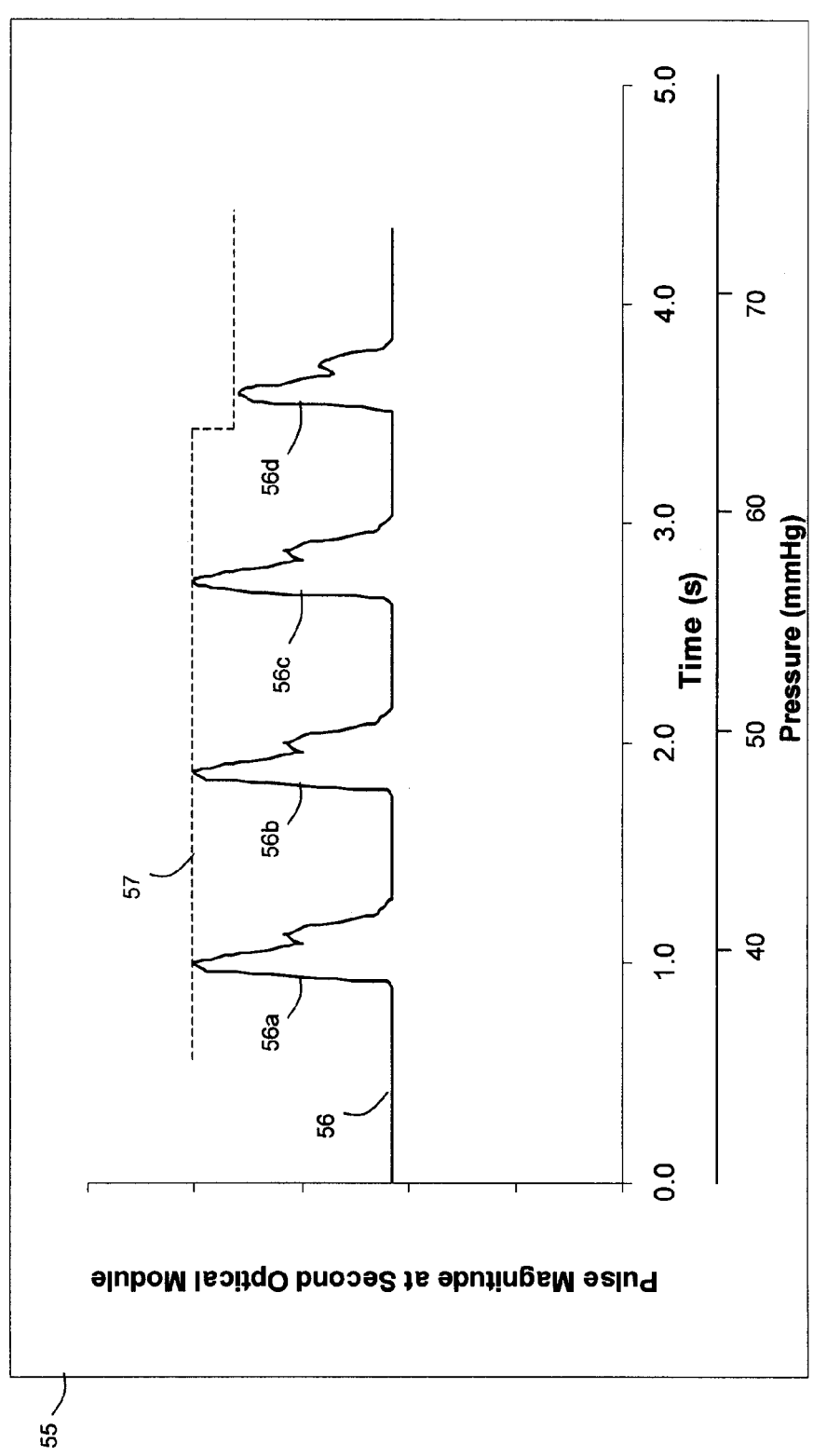
FIG. 4A is a graph of a time-dependent waveform, used to determine the diastolic blood pressure, that features a stepwise decrease in intensity of blood pressure pulses caused by the pressure pulse.

FIG. 4A indicates the principle of the first measurement. This measurement depends on the fact that the magnitude of the optically measured pulse depends on the blood volume. The figure shows a graph 55 with a waveform 56 measured by the second optical module. The waveform 56 features four consecutive pulses 56a–d. As the pressure pad imparts a pressure to the artery (starting at about 40 mmHg at the 1-second point in the graph), the artery is gently compressed. While the pressure imparted by the pressure pulse is between 40 and 60 mmHg, the diastolic pressure exceeds this value and blood flow is not restricted. Thus the first three pulses 56a–c in the waveform 56, as measured by the second optical module, have similar amplitudes. When the pressure reaches about 66 mmHg (after about 3.6 seconds) the pressure imparted by the pressure pulse begins to exceed the diastolic pressure. This slightly restricts the passing blood volume and consequently reduces the amplitude of the forth pulse 56d. A line 57 in the graph 55 indicates this stepwise decrease in pulse amplitude. During a measurement, the microprocessor analyzes the stepwise decrease in pulse magnitude to determine the diastolic pressure. This value is stored in a computer memory and processed in more detail as described below.

Figure 4B:
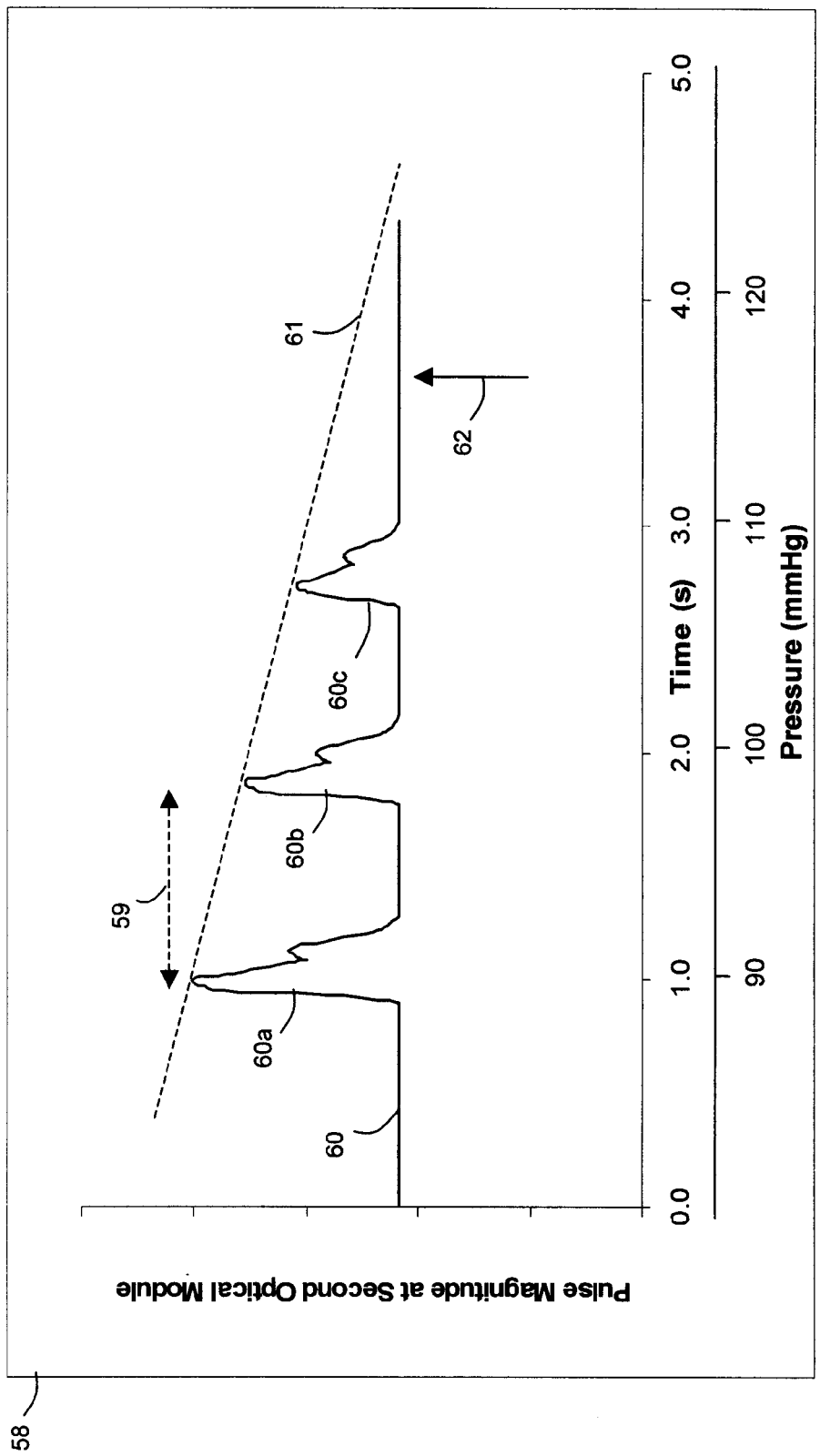
FIG. 4B is a graph of a time-dependent waveform, used to determine the systolic blood pressure, that features a linear decrease in intensity of blood pressure pulses caused by the pressure pulse.

FIG. 4B indicates the principle of the second measurement. The figure shows a graph 58 that includes a waveform 60 with three consecutive pulses 60a–c. For this figure the applied pressure is greater than the diastolic pressure. As the pressure pad imparts a second pressure pulse to the artery (starting at the 1-second point in the graph), the pulse magnitude decreases in a linear fashion as the applied pressure increases. A line 61 in the graph 58 indicates the linear decrease in pulse amplitude. When the pressure exerted by the pad exceeds the systolic pressure, blood ceases to flow and the pulse, normally present at a temporal value indicated by the arrow 62, is not detectable. This occurs after about 3.7 seconds or about 117 mmHg. During a measurement, the microprocessor analyzes the systematic decrease in pulse magnitude and the spacing between the pulses, indicated respectively by the line 59, and uses these to extrapolate a pressure at which blood flow is completely restricted. This indicates the systolic pressure. Once determined, the microprocessor stores this value in a computer memory combines this measurement with first measurement of diastolic pressure to determine the patient's maximum and minimum blood pressures.

The device determines beat-by-beat blood pressure by processing the systolic and diastolic blood pressures with a waveform, measured by either the first or second optical modules, in the absence of a pressure pulse. This processing involves a simple linear transformation wherein the baseline of the waveform is mapped to the diastolic pressure, and the average height of a train of pulses is mapped to the systolic pressure. The linear transformation algorithm determines points in between these two extremes.

Referring again to FIG. 1, in detecting the above-described pulses for both the first and second measurements, the optical detection systems 14b, 16b receive reflected radiation from the light source systems 14a, 16a and in response generate photocurrent that passes through an electrical lead 28 to an amplifier 18. The amplifier 18 receives the signal, amplifies it to a measurable level, and then sends it to an electrical filter 20 to remove noise and other artifacts that may affect the measurement's accuracy. The electrical filter 20 passes the signal to an analog-to-digital converter 22 that converts it to a digital signal, which the microprocessor 24 then processes as described in detail below. The microprocessor 24 analyzes the signals originally generated during the first, second, and third measurements by the first and second optical modules 14, 16 to yield a time-dependent blood pressure trace (as shown, for example in FIG. 5). A computer memory 25 in electrical contact with the microprocessor 24 stores the data, which can additionally be passed through a serial port 27 to, e.g., a display or computer for further processing.

Figure 2A:
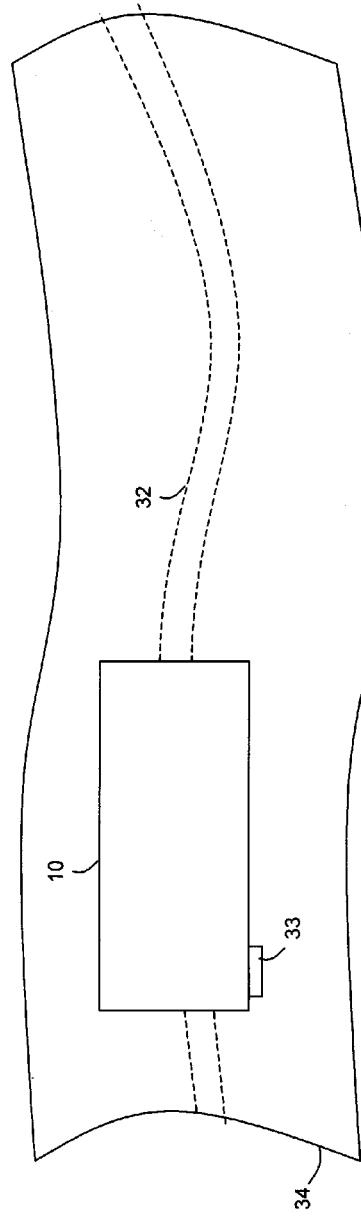
FIG. 2A is a schematic, overhead view of the blood pressure-measuring device of FIG. 1 measuring blood pressure from a patient's arm.
Figure 2B:
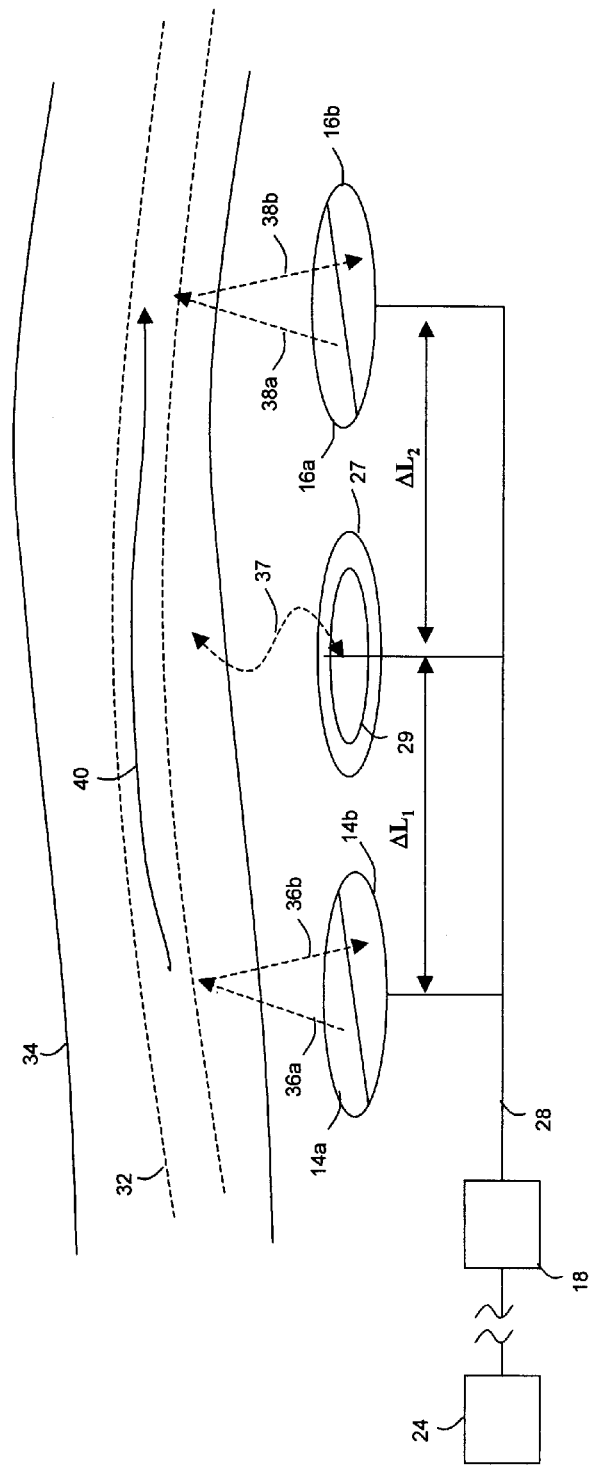
FIG. 2B is a schematic, side view of optical modules and the pressure pad within the blood pressure-measuring device of FIG. 1 measuring blood pressure from a patient's arm.

FIGS. 2A and 2B show in more detail how the above-described blood-pressure monitoring device 10 measures a patient's time-dependent blood pressure. In general, the device 10 is hand-held and can measure blood pressure from any part of the patient's body. During a measurement, a medical professional places the device 10 over a body part 34 (e.g., an arm) of a patient. The medical professional orients the device 10 so that the optical modules 14, 16 are proximal to the patient's artery 32. Once the device 10 is oriented in this way, the medical professional presses a button 33 that initiates the blood-pressure measurement. As described above, the measurement features first, second, and third measurements that determine the patient's real-time, beat-by-beat blood pressure. Each measurement is a reflective optical measurement wherein a light source system 14a in a first optical module emits radiation 36a ($\lambda$=600, 850 nm) that blood in the artery 32 partially absorbs and reflects. An optical detection system 14b receives the reflected radiation 36b and generates a photocurrent-induced waveform that passes to an amplifier 18 and, ultimately, a microprocessor 30 for processing. Blood flows in the artery 32 along a path indicated by an arrow 40. Both the first 14 and second optical modules continually measure the waveforms according to the first, second, and third measurements described above.

For both the first and second measurements, the microprocessor analyzes a calibrated pressure from the mechanical module in combination with a waveform from the optical modules. As described above, the microprocessor determines the diastolic or systolic pressure by extrapolating the systematic or stepwise decrease in pulse intensity and comparing it to the exerted pressure. Alternatively, the microprocessor can fit the waveform containing the pulses with a mathematical function to more accurately determine the diastolic and systolic pressures. The microprocessor can also compare the pulse amplitude measured by the first optical module (which is typically not affected by the pressure pulse) with that measured by the second optical module (which is strongly affected by the pressure pulse) to determine the pressures at which blood flow is impeded. In some circumstances, the pulse amplitude measured by the first optical module may even increase at the onset of the diastolic pressure as blood flow builds up, and thus blood volume increases, due to the imparted pressure. This phenomenon can be detected and additionally used to determine the diastolic pressure.

The second optical module has suitable sensitivity to rapidly and accurately detect very slight changes in the pulse magnitude. This means that the pressure pad can quickly increase pressure on the artery while the module accurately measures blood flow and pressure. Ultimately, this reduces the time for a typical blood-pressure measurement (usually about 2 minutes) to just a few seconds. And the accuracy is dramatically increased, as the optical module, measuring the magnitude of the pulse, is much more sensitive than a conventional pressure sensor embedded in a cuff.

Figure 5:
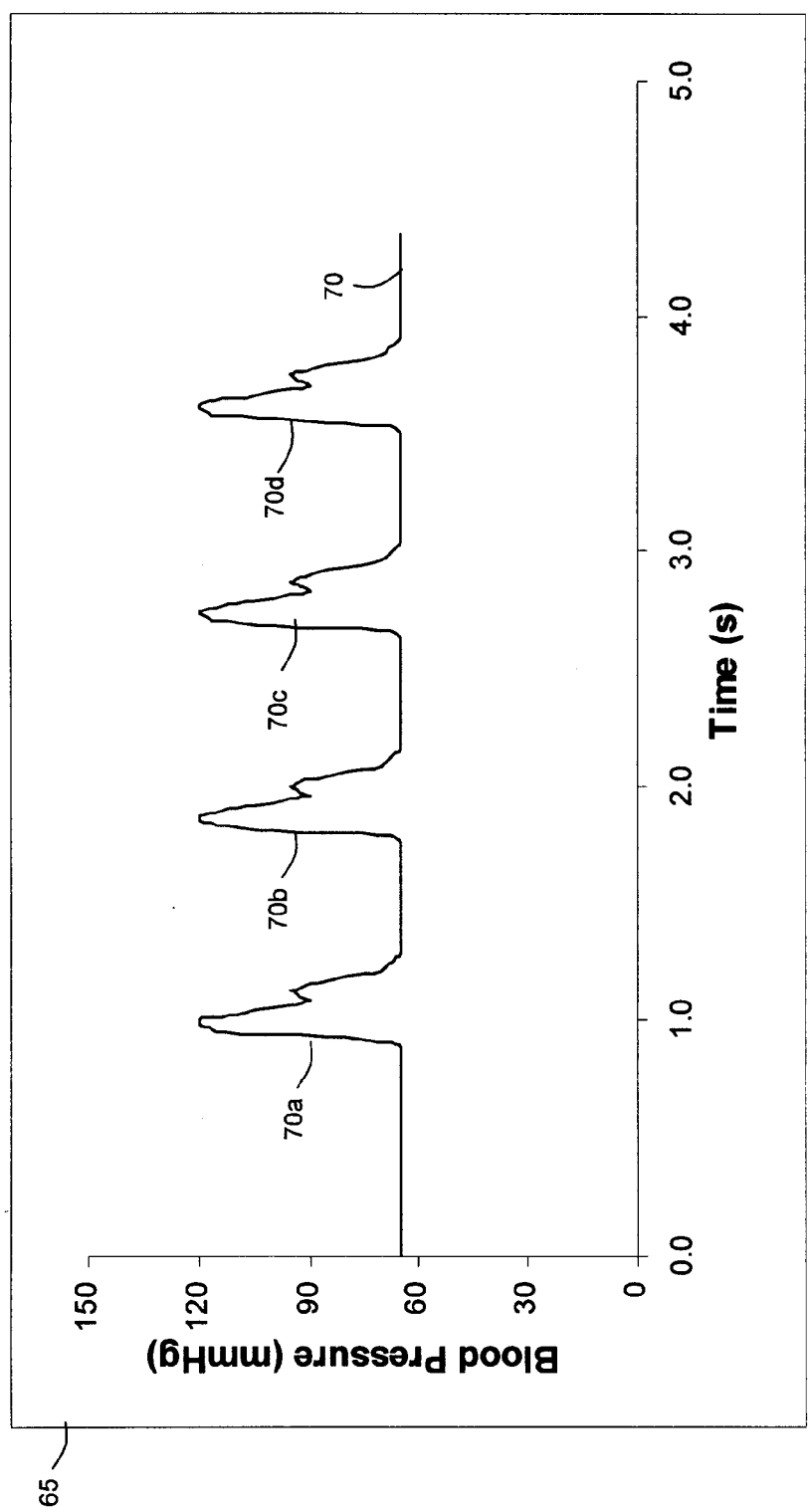
FIG. 5 is a graph of time-dependent blood pressure measured by processing the time-dependent waveforms of FIGS. 3, 4A, and 4B.

FIG. 5 shows a graph 65 that plots the beat-to-beat blood pressure resulting from the first, second, and third measurements. The graph 65 features a waveform 70, indicating the patient's real-time, beat-by-beat blood pressure. The waveform 70 includes a baseline that represents the diastolic blood pressure (in this case about 66 mmHg). As the patient's heart beats, blood volume forces through the measured artery, increasing the blood pressure. A first pulse 70a in the waveform 70 indicates this increase. The maximum value of the pulse (in this case about 117 mmHg) represents the systolic blood pressure. As the blood volume passes through the artery, the pressure decreases and returns to the baseline, diastolic value. This cycle is repeated, as represented by additional pulses 70b–d in the trace 62, as the patient's heart continues to beat.

Figure 6:
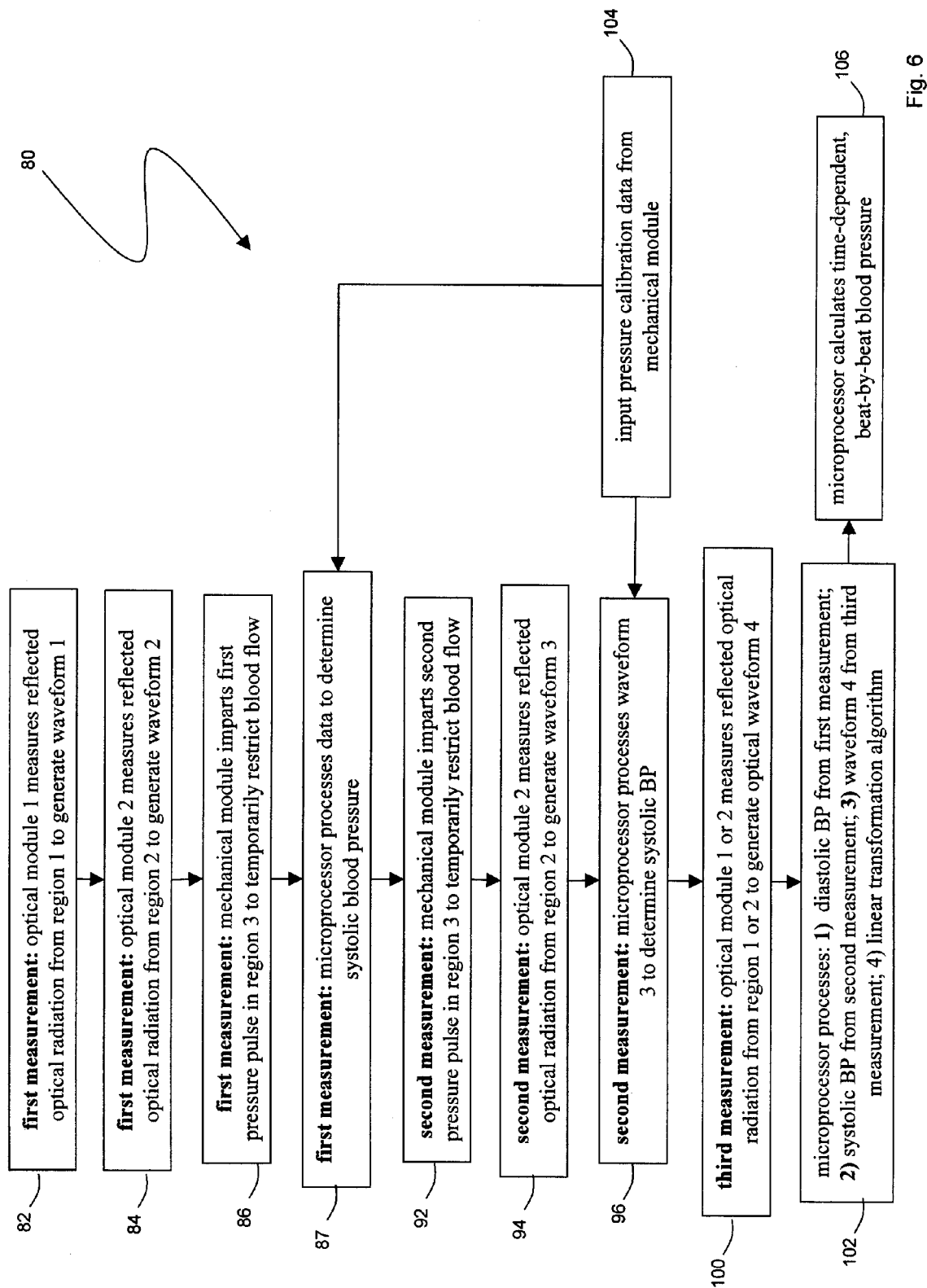
FIG. 6 is a flow chart describing an algorithm used by a microprocessor in the blood-pressure measuring device of FIG. 1 to calculate a patient's time-dependent blood pressure.

FIG. 6 shows a flow chart that summarizes a process 80 managed by the microprocessor to calculate blood pressure from the optical measurements made by the device of FIG. 1. The process 80 uses the reflective optical measurements of the first measurement to generate waveforms 1 and 2 from, respectively, regions 1 and 2 on the patient (step 82, 84). The mechanical module then imparts a first pressure pulse that, when equivalent to the diastolic pressure, decreases the amplitude of a pulse in the waveform (step 86) measured by the second optical sensor. The microprocessor processes these data with input pressure calibration data from the mechanical module (step 104) to determine to determine the diastolic blood pressure (step 87).

The process 80 then uses the mechanical module to impart a second pressure pulse in region 3 to temporarily restrict blood flow (step 92). The second optical module then measures a waveform from region 2 (step 94), and processes this waveform with input pressure calibration data from the mechanical module (step 104) to determine the systolic blood pressure (step 96).

Finally, the process 80 uses a third measurement to measure, with either the first or second optical module, a waveform from either region 1 or 2 (step 100). Using a linear transformation algorithm, the microprocessor then processes: 1) the diastolic blood pressure from the first measurement; 2) the systolic blood pressure from the second measurement; and 3) the waveform from third measurement (step 102). Once processed these data yield a time-dependent, beat-by-beat blood pressure (step 104).

Other embodiments are within the scope of the invention. Particular embodiments include blood pressure-measuring devices that accurately measure blood pressure without using a mechanical module for delivering a pressure pulse.

In embodiments, these devices use an electrical configuration (e.g., amplifier, filter, microprocessor, analog-to-digital coverter, memory module) similar to that shown in FIG. 1 and are enclosed in a hand-held form factor. In this way they can measure blood pressure from any part of a patient's body.

Such devices, for example, can use non-invasive sensors that measure the time-dependent dynamics of flowing blood and process these data with mathematical algorithms to determine blood pressure. In one embodiment, the mechanical module (27) of the device of FIG. 1 is replaced with an electrical impedance (EI) sensor that features an electrode pair that measures the change of electrical impedance of the underlying arterial segment. EI sensors are typically used in impedance plethysmography as a way of determining changing tissue volumes in an underlying tissue body. The EI sensor measures electric impedance at the tissue surface by transmitting a small amount of alternating current (typically between 20–100 kHz) through the underlying tissue. The tissue includes components such as bone and skin that have a static (i.e. time invariant) impedance, and flowing blood, which has a dynamic (i.e. time varying) impedance. Blood has a well-defined resistivity of about 160 Ω-cm. Impedance, defined as electrical resistance to alternating current, will therefore vary as the volume of blood in the tissue changes with each heartbeat. Measurements made with the EI sensor, following processing with a firmware algorithm, yield an impedance waveform that features "pulses" indicating the time-dependent volumetric flow of blood. When the EI sensor replaces the thin-film pressure sensor, the separation between pulses in the impedance waveform and those in the optical waveform yield a difference in pressure ($\Delta P$) between the systolic and diastolic pressure. Combined with the below-described calibration process, the magnitude of each pulse can be correlated to the systolic pressure. The entire impedance waveform can therefore be used in place of the pressure waveform to determine systolic and diastolic pressure.

In addition to this sensor, the blood pressure-measuring device can include a pair of optical modules, similar to those described in FIG. 1, that measure the time-dependent variation in arterial diameter caused by blood flow. These data, along with data generated by the EI sensor, can be processed with a mathematical algorithm to determine blood pressure.

The mathematical algorithm used for this calculation can take many forms. For example, the paper entitled "Cuffless, Continuous Monitoring of Beat-to-Beat Pressure Using Sensor Fusion" (Boo-Ho Yang, et al., submitted to the IEEE Transactions on Biomedical Engineering, 2000) describes an algorithm based on a two-dimensional Navier-Stokes differential equation that models pulsatile flow of a Newtonian liquid (e.g., blood) through an elastic, deformable cylindrical vessel (e.g., an artery). This differential equation can be solved in a number of different ways, and is shown below in Equation 1:

$$\frac{\partial u}{\partial t} + w\frac{\partial u}{\partial r} + u\frac{\partial u}{\partial z} = -\frac{1}{\rho}\frac{\partial P}{\partial z} + v\left(\frac{\partial^2 u}{\partial r^2} + \frac{1}{r}\frac{\partial u}{\partial r} + \frac{\partial^2 u}{\partial z^2}\right)$$

$$\frac{\partial w}{\partial t} + w\frac{\partial w}{\partial r} + u\frac{\partial w}{\partial z} = -\frac{1}{\rho}\frac{\partial P}{\partial r} + v\left(\frac{\partial^2 w}{\partial r^2} + \frac{1}{r}\frac{\partial w}{\partial r} + \frac{\partial^2 w}{\partial z^2} - \frac{w}{r^2}\right)$$

$$\frac{1}{r}\frac{\partial}{\partial r}(rw) + \frac{\partial u}{\partial z} = 0$$

(1)

In Equation 1, r, θ, z are the cylindrical coordinates of an arterial segment. P denotes pressure, ρ density, ν kinematic viscosity, and u(r,z,t) and w(r,z,t) denote the components of velocity in the axial (z) and radial (r) dimensions, respectively.

Equation 1 can be solved to generate a mathematical expression that, using inputs from the first and second optical modules and the EI sensor, yields a patient's time-dependent, beat-by-beat blood pressure (e.g., P(t)).

In other embodiments, for example, simplified versions of the blood pressure-monitoring devices described above can be used to estimate a patient's blood pressure. In one embodiment, a pair of optical modules, as described above, measure blood flow at two separate points on a patient. A microprocessor processes these data to determine a time difference ($\Delta T$) for blood to flow from the first point to the second point. The microprocessor detects the separation between the peak values of two sequential pulses (e.g., 52a and 54a in FIG. 3) and uses an internal real-time clock to convert this separation into a time value. These parameters are then processed according to the algorithm described below to determine blood flow rate that is then used to determine the difference between systolic and diastolic pressure.

Specifically, for this measurement, the microprocessor uses a mathematical algorithm based generally on Bernoulli's equation to estimate blood pressure from the time-dependent data collected above. Bernoulli's equation states that pressure is inversely proportional to flow rate. For the above-described system, Bernoulli's equation is modified to generate a model that accounts for flow of an incompressible, Newtonian fluid (i.e. blood) through a deformable, cylindrically shaped vessel (i.e. an artery). The model depends on density, viscosity, fluid flow rate, and pressure of the blood, and the mechanical properties (e.g., diameter, wall thickness, elasticity) of the artery. The model uses standard values for blood density, viscosity, and for mechanical properties of the artery. The model also considers the artery to be elastic and the flow of blood to be pulsatile, i.e. not steady state, and takes into account Poiseuillei's law, which describes a Newtonian liquid propagating in a tube. According to Poiseuillei's law, the linear flow (Q) through a tube of length L and radius r relates to a pressure gradient ($\Delta P$) and the viscosity (v) of the flowing liquid (i.e. blood):

$$\Delta P = 16v\Delta LQ/r^2 \quad (2)$$

Equation 2 can be used to estimate the pressure difference between systolic and diastolic pressure. For this approximation, the linear fluid flow rate Q is measured using the first and second optical modules described above in FIGS. 1, 2A, and 2B. This is done by dividing $\Delta L$, the length separating these modules (typically 5 cm in the device of FIG. 1), by time difference between pulses monitored by the first and second optical modules ($\Delta T$ in FIG. 3). Estimated values for Equation 2 are r (the radius of the blood vessel, typically 0.5 mm at the arm), and ν (the viscosity of blood, typically 0.04 poise). Using these values, ΔP, i.e. the pressure difference between diastolic and systolic blood pressure, can be estimated. These data can be used, e.g., in combination with calibration data to determine a patient's blood pressure.

FIG. 7, for example, shows an all-optical, hand-held blood-pressure monitoring device 110 according to an alternate embodiment of the invention that provides a cuffless, non-invasive, beat-by-beat measurement of blood pressure. The device 110 is similar to that shown in FIG. 1, but lacks a mechanical module (27 in FIG. 1) that delivers the pressure pulse to the underlying artery. For this device, the blood-pressure measurement is made with a pair of optical modules 114, 116 that each features a light source system 114a, 116a with separate light-emitting diodes ("LEDs"). The optical properties of the optical modules, and the pulses they detect from the underlying flowing blood, are similar to those described with respect to FIG. 1.

In detecting the above-described pulse, the optical detection systems 114b, 116b receive reflected radiation from the light source systems 114a, 116a and generate radiation-induced electrical current signal that passes through an electrical lead 126 to an amplifier 118. The amplifier 118 receives the signal, amplifies it to a predetermined level, and then passes the signal to an electrical filter 120 to remove noise and other artifacts that may affect accuracy in the measurement. The electrical filter 120 passes the signal to an analog-to-digital converter 122 that converts it to a digital signal, which a microprocessor 124 then processes as described below to determine blood pressure. The microprocessor 124 analyzes the signals originally generated by the first and second optical modules 114, 116 to yield a time-dependent blood pressure trace (as shown, for example in FIG. 5) that a memory module 125 stores. The memory module 125 can additionally send these data through a serial port 127 to, e.g., a display or computer for further processing. A button 133 in electrical communication with the microprocessor 124 initiates the blood-pressure measurement.

Figure 8A:
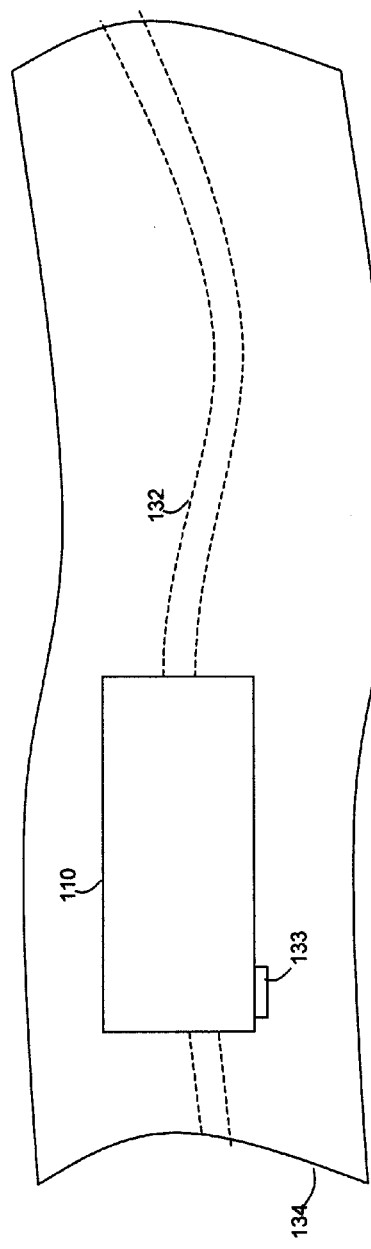
FIG. 8A is a schematic, overhead view of the blood-pressure measuring device of FIG. 7 measuring blood pressure from a patient's arm.
Figure 8B:
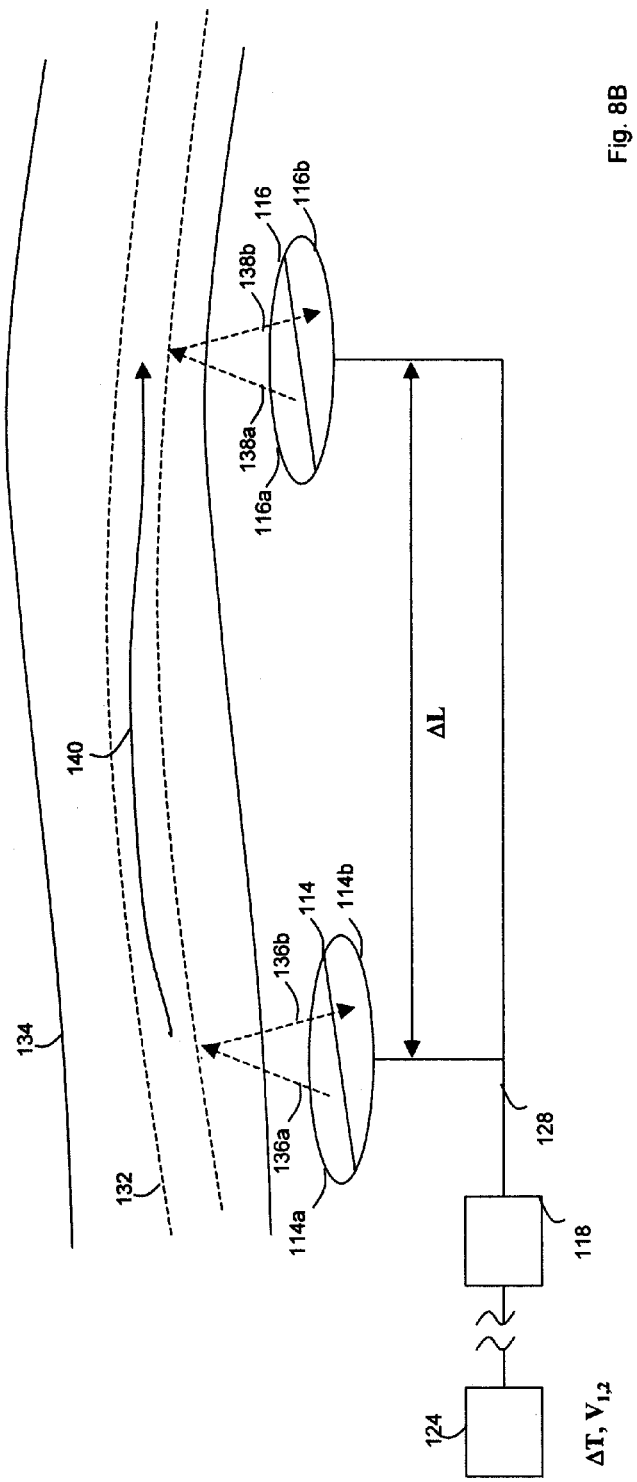
FIG. 8B is a schematic, side view of optical modules within the blood-pressure measuring device of FIG. 7 measuring blood pressure from a patient's arm.
Figure 9:
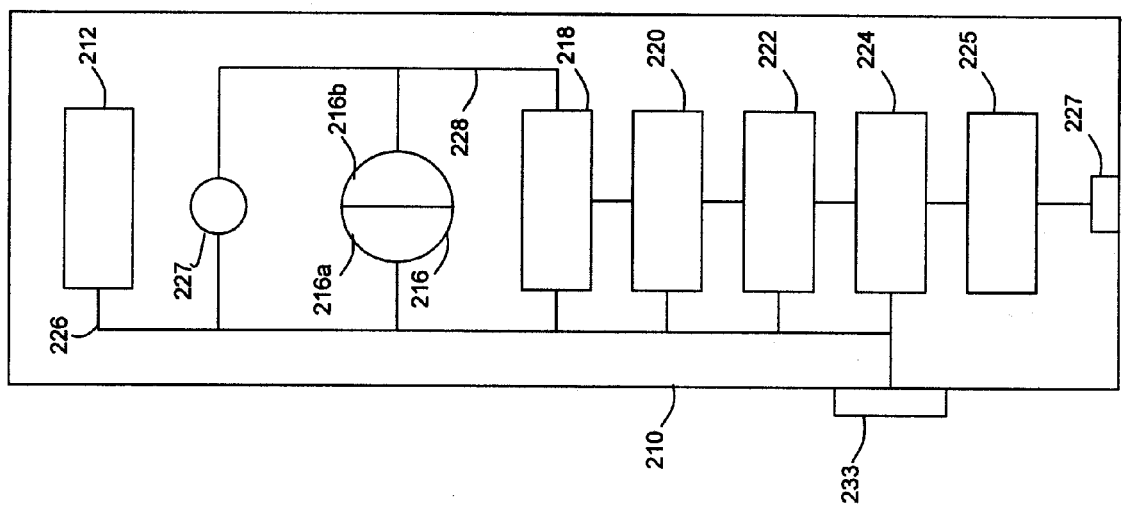
FIG. 9 is a schematic, overhead view of a blood-pressure measuring device featuring a single optical module and a thin-film pressure sensor according to an alternative embodiment of the invention.

FIGS. 8A and 8B show in more detail how the above-described blood-pressure monitoring device 110 measures time-dependent blood pressure from a patient. Like the device described in FIG. 1, the device 110 is hand-held and can measure blood pressure from any part of the patient's body. During a measurement, a medical professional places the device 110 over a body part 134 (e.g., an arm) of a patient. The medical professional orients the device 110 so that the optical modules 114, 116 are proximal to the patient's artery 132. Once the device 110 is oriented in this way, the medical professional presses a button 133 that initiates the blood-pressure measurement. As described above, the measurement is optical and operates in a reflection mode wherein a light source system 114a in a first optical module emits radiation 136a that blood in the artery 132 partially absorbs and reflects. An optical detection system 114b receives the reflected radiation 136b and generates a current pulse signal that passes to an amplifier 118 and, ultimately, a microprocessor 130 for processing. Blood flows in the artery 132 along a path indicated by an arrow 140. When the blood reaches the second optical system 116 the device 110 automatically repeats the above-described measurement. The separation between the two optical modules (ΔL in the figure) is known. The microprocessor 124 processes the signals from the first and second optical modules to determine the time difference (ΔT), flow rate (ΔL/ΔT), and blood volume $V_{1,2}$. The microprocessor then processes these parameters as described above to estimate the different between systolic and diastolic blood pressure.

The device shown in FIGS. 7, 8A, and 8B may also require the patient to input blood pressure calibration data, such as a recent blood pressure measurement, through the serial port 127. The calibration data are use to further enhance the accuracy of the measurement.

FIGS. 9, 10A, 10B, and 11 show another embodiment of the invention that measures a patient's blood pressure without applying a pressure pulse. In this approach, a device 210 includes a single optical module 216 and a thin-film pressure sensor 227 spaced by a distance ΔL. The device 210 is hand-held in the embodiment shown in the figures. Alternatively, the device is worn on the patient's body using, e.g. a watch-like form factor where the optical module 216 attaches to the patient's finger and the thin-film pressure sensor 227 attaches to the patient's wrist. The optical module 216 is similar to the optical modules described above with reference to FIGS. 2A, 2B, 8A, and 8B, and includes a light source system 216a and an optical detection system 216b. The thin-film pressure sensor 227 is a flexible, thin plastic film filled with a compound featuring a pressure-sensitive electrical resistance. Pressure applied to a measurement region causes the resistance to decrease in a linear manner. Such a sensor is manufactured by Tekscan of South Boston, Mass. (www.tekscan.com) and described in detail in U.S. Pat. No. 6,272,936, the contents of which are incorporated herein by reference.

To measure pressure, both the thin-film pressure sensor 227 and optical module 216 generate signals that pass through a series of electronics similar to those described above. These include an amplifier 218 that receives signals and amplifies them with a predetermined gain, and an electrical filter 220 that removes noise and other artifacts that may affect accuracy in the measurement. The electrical filter 220 passes the signals to an analog-to-digital converter 222 that converts them to a digital signal, which the microprocessor 224 then processes as described below to determine blood pressure. A memory module 225 stores the data before and after processing.

During manufacturing, the thin-film pressure sensor 227 typically has to be calibrated to covert its signal (i.e., a variable resistance or the corresponding voltage measured by the analog-to-digital converter 222) into a pressure value. To calibrate this component, a range of well-known pressures is applied to the sensor and programmed into the microprocessor 224. Firmware running in the microprocessor performs a simple linear calibration using these values. Once this is complete, the microprocessor 224 can convert a signal from the pressure sensor 227 into an actual pressure reading.

Figure 11:
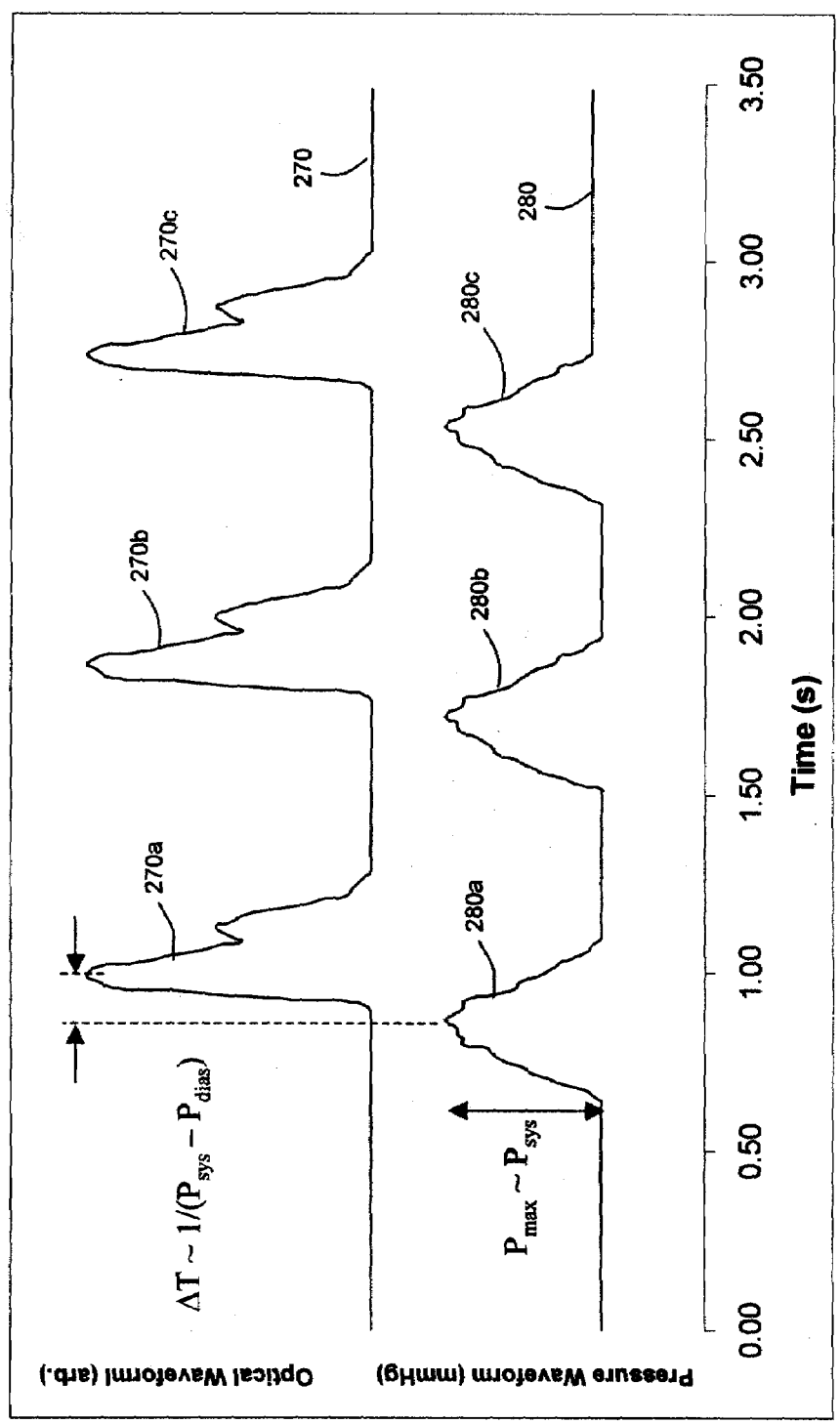
FIG. 11 is a graph that shows, respectively, time-dependent waveforms measured by the optical module and thin-film pressure sensor of FIG. 9.

During a measurement, the device 210 is oriented so that both the optical module 216 and the thin-film pressure sensor 227 are proximal to the patient's body 234 and oriented to measure blood flowing through an underlying artery 232. The patient presses a button 233 that initiates the blood-pressure measurement. Alternatively, firmware running on the microprocessor 224 can automatically initiate the measurement. Blood flowing following a heartbeat causes pressure in the artery 232 to rise from the diastolic pressure ($P_{dias}$) to the systolic pressure ($P_{sys}$). For each heartbeat, the thin-film pressure sensor detects a "pressure waveform" featuring a "pressure pulse" with a magnitude indicating a heartbeat-induced rise in pressure. FIG. 11 shows this pressure rise is proportional to the systolic pressure. As blood flows through the artery 232, it is measured at a later time by the optical module 216. An optical detection system 214b receives the reflected radiation 236b and generates an "optical waveform" featuring an "optical pulse" similar to that described above, corresponding to each heartbeat.

FIG. 11 shows an optical waveform 270 that includes a series of optical pulses 270a–c, and a pressure waveform 280 that includes a series of pressure pulses 280a–c. The microprocessor analyzes these waveforms 270, 280 as described below to determine beat-to-beat blood pressure.

The time difference between when the thin-film pressure sensor 227 measures a pressure pulse and when the optical module 216 measures a corresponding optical pulse is the time it takes blood to flow along a length $\Delta L$ of the artery 240. This time, shown in FIG. 11 as $\Delta T$, yields the flow rate ($\Delta T=1/Q\sim 1/(P_{sys}-P_{dias})$). The microprocessor calculates $\Delta T$ by measuring the peak intensity of both the optical and pressure pulses, and then calculating the time lag between these pulses.

An additional calibration process is typically required to convert Q into a pressure value as described above with reference to Eqn. 2. To calibrate the device 210, a patient attaches a stand-alone cuff to their arm prior to making an actual measurement. The cuff features a serial output that sends pressure values to the device 210 as it inflates. This cuff is only used during calibration. To 'set up' the system, the user inflates the cuff, which in turn applies pressure to the arm and underlying artery. Pressure gradually increases until it first meets the patient's diastolic pressure. At this point, the cuff compromises blood flow in the artery, and the pulses in the optical waveform begin to decrease. This determines $P_{dias}$. As the pressure increases to the systolic pressure, the signal measured by both the thin-film pressure sensor and the optical module decrease to 0. This is because temporarily stops flowing through the artery because of the applied pressure, and thus no signals are measured. This determines $P_{sys}$. The patient then removes the cuff, at which point the device begins measuring $\Delta T$ (and thus Q).

With this value, Eqn. 2 can be reduced to:

$$\Delta P = P_{sys} - P_{dias} = X_1 Q \quad (3)$$

where $X_1$ is a calibration factor that accounts for blood viscosity (v), the radius of the underlying artery (r), and the length separating the pressure sensor and optical module ($\Delta L$). Using $X_1$, the microprocessor analyzes a simple measurement of $\Delta T$ to determine $\Delta P = P_{sys} - P_{dias}$. In addition, the calibration process can be used to correlate the maximum pulse magnitude in the pressure waveform to $P_{sys}$:

$$P_{max} = X_2 P_{sys} \quad (4)$$

The calibration factors $X_1$, $X_2$ are automatically calculated by the microprocessor during the set-up process and used for all on-going measurements.

Once the calibration is performed, cuff is removed, and device 210 measures flow rate to determine systolic and diastolic pressure using the calibration factors as described above. Measurements can be performed continuously without any discomfort to the patient because no cuff is required.

Still other embodiments are within the scope of the invention. For example, the placement of the above-described optical, mechanical, and electrical modules can be modified to change the form factor of the device. Or the modules can be separated and not included in a single handheld device. For example, the measuring modules may be includes in an arm-worn patch, while the electronics that process data from these sensors may be included in a belt-worn pack. Other configurations of the above-described optical, mechanical, and electrical sensors are also within the scope of the invention.

The device can also use algorithms other than those described above to process data measured by the module. These algorithms are typically based on the equations described above, but may vary in their form. Or the device can consolidate various electronic components shown in FIG. 1 into a single silicon-based device. For example, the silicon-based device can include filters, memory, and an analog-to-digital converter.

In still other embodiments, the above-described device may include a wireless transmitter to send blood-pressure data from the patient to a central computer system. This type of "telemedicine" is possible since the blood pressure-monitoring device of the invention does not rely on a cuff that historically has made telemedicine impractical for blood-pressure measurements. Short-range wireless transmitters that can be used include those based on 802.11 and Bluetooth wireless protocols. These transmitters, for example, can send information from a body-worn device to an external wireless hub, which then transmits the information over a nationwide wireless network. Very short-range part-15 wireless transmitters can also be used for this purpose. In this case, "part-15" refers to a conventional low-power, spread-spectrum, short-range wireless protocol, such as that used in cordless telephones. Long-range transmitters include those used in nationwide terrestrial radio or satellite networks. Such transmitters include those that operate on the following networks: Sprint (CDMA), Verizon (CDMA), ATT (GSM/GPRS), T-Mobile (GSM/GPRS), Cingular (Mobitex), Motient (DataTac), Orbcomm (Orbcomm Satellite). Other wireless networks and protocols, such as GPS for determining the patient's location, can also be used. In other embodiments, the antennae used to transmit the blood pressure information or receive the GPS signals are embedded in the device, rather than being exposed.

Once transmitted, the information may be sent to an Internet-accessible software piece for analysis and display. The Internet-accessible software piece typically includes a gateway software piece for extracting data from a wireless network, a database for storing the data, and an interface that includes a "patient" interface that displays a patient's blood-pressure data, and a "care provider" interface that displays data associated with a group of patients.

Still other embodiments are within the scope of the following claims.

The invention claimed is:

1. A hand-held device for monitoring a patient's blood pressure, comprising:
    a hand-held component configured to be held proximal to the patient's skin;
    a first optical module operating in a reflective mode and comprised by the hand-held component, the first optical module comprising a first optical source component configured to generate optical radiation and a first optical sensor configured to detect reflected radiation from the patient and, in response, generate a first set of information when the hand-held component is held proximal to the patient's skin;
    a second optical module operating in a reflective mode and comprised by the hand-held component, the second optical module comprising a second optical source component configured to generate optical radiation and a second optical sensor configured to detect reflected radiation from the patient and, in response, generate a second set of information when the hand-held component is held proximal to the patient's skin;

an electrical sensor comprised by the hand-held component and comprising an electrode pair configured to generate a third set of information when the hand-held component is held proximal to the patient's skin; and a processing module, comprised by the hand-held component, and configured to receive the first, second, and third sets of information, the processing module comprising a processor that calculates a first time-dependent property from components of the first set of information and the second set of information and a second time-dependent property from the third set of information and at least one of the first and second sets of information and compares the first and second time-dependent properties to a mathematical model to calculate a blood pressure value.

2. The device of claim 1, wherein the third set of information generated by the electrical sensor is a time-dependent electrical waveform generated in response to a body-generated electrical signal.

3. The device of claim 1, wherein the hand-held component further comprises an analog-to-digital converter connected to the processing module.

4. The device of claim 1, wherein at least one of the first and second optical source components comprises a first LED that generates visible radiation, and a second LED that generates infrared radiation.

5. The device of claim 4, wherein at least one of the first and second optical sensors is a photodiode.

6. The device of claim 5, wherein the photodiode is configured to generate a photocurrent after detecting radiation generated by the first LED and the second LED.

7. The device of claim 6, wherein the hand-held component further comprises an analog-to-digital converter connected to the processing module and configured to receive and process the photocurrent.

8. The device of claim 1, wherein the processor further comprises computer-readable firmware that processes the first set of information to additionally determine pulse oximetry and heart rate.

9. The device of claim 1, wherein the hand-held component further comprises a serial interface.

10. The device of claim 9, wherein the serial interface is configured to send information to an external device.

11. The device of claim 9, wherein the serial interface is configured to accept calibration information.

12. A method for measuring a blood pressure value from a patient, comprising the steps of:

1) holding a hand-held component proximal to the patient's skin, the hand-held component comprising: i) a first optical component comprising a first optical source component configured to emit optical radiation and a first optical sensor configured to detect reflected radiation and, in response, generate a first set of information while the hand-held component is held proximal to the patient's skin; ii) a second optical component comprising a second optical source component configured to emit optical radiation and a second optical sensor configured to detect reflected radiation and, in response, generate a second set of information while the hand-held component is held proximal to the patient's skin; iii) an electrical component comprising an electrode pair configured to generate a third set of information while the hand-held component is held proximal to the patient's skin; and iv) a processor, comprised by the hand-held component, and operating an algorithm configured to process the first, second, and third sets of information;

2) initiating a measurement wherein the first optical component generates the first set of information, the second optical component generates the second set of information, and the electrical component generates the third set of information; and 3) processing the first, second, and third sets of information with the processor by calculating a first time-dependent property from components of the first and second sets of information, and calculating a second time-dependent property from the third set of information and at least one of the first and second sets of information, and comparing the first and second time-dependent properties to a mathematical model to calculate a blood pressure value.

13. A method for analyzing a blood pressure value from a patient, comprising the steps of:

1) holding a hand-held component proximal to the patient's skin, the hand-held component comprising: i) a first optical component comprising a first optical source component configured to emit optical radiation and a first optical sensor configured to detect reflected radiation and, in response, generate a first set of information while the hand-held component is held proximal to the patient's skin; ii) a second optical component comprising a second optical source component configured to emit optical radiation and a second optical sensor configured to detect reflected radiation and, in response, generate a second set of information while the hand-held component is held proximal to the patient's skin; iii) an electrical component comprising an electrode pair configured to generate a third set of information while the hand-held component is held proximal to the patient's skin; and iv) a processor, comprised by the hand-held component, and operating an algorithm configured to process the first, second, and third sets of information;

2) initiating a measurement wherein the first optical component generates the first set of information, the second optical component generates the second set of information, and the electrical component generates the third set of information;

3) processing the first and second sets of information with the processor by calculating a first time-dependent property from components of the first and second sets of information and processing the third set of information and at least one of the first and second sets of information with the processor by calculating a second time-dependent property from components of the third set of information and at least one of the first and second sets of information and comparing the first and second time-dependent properties to a mathematical model to calculate a blood pressure value; and 4) wirelessly transmitting the blood pressure value to an external receiver.

14. The method of claim 13, further comprising the step of transmitting the blood pressure value to an Internet-accessible computer system.

15. The method of claim 13, further comprising the step of transmitting the blood pressure value to a central computer system.

16. A device for monitoring a patient's blood pressure, comprising:

a first optical module comprising a first optical source component configured to generate optical radiation and a first optical sensor configured to detect radiation from the patient and, in response, generate a first set of information;

a second optical module comprising a second optical source component configured to generate optical radiation and a second optical sensor configured to detect radiation from the patient and, in response, generate a second set of information;

an electrical sensor comprising an electrode pair configured to generate a third set of information; and a processing module configured to receive the first, second, and third sets of information, the processing module comprising a processor that calculates a first time-dependent property related to a time-dependent variation in arterial properties from components of the first set of information and the second set of information and a second time-dependent property related to a blood pressure change from the third set of information and at least one of the first and second sets of information and compares the first and second time-dependent properties to a mathematical model to calculate a blood pressure value.

* * * * *